United States Patent
Ching

(10) Patent No.: US 6,719,741 B2
(45) Date of Patent: Apr. 13, 2004

(54) URINE GUIDE DEVICE FOR FEMALES

(76) Inventor: Ou Feng Ching, 3F, No. 441 Sung-Shan Road, Taipei (TW)

( * ) Notice: Subject to any disclaimer, the term of this patent is extended or adjusted under 35 U.S.C. 154(b) by 32 days.

(21) Appl. No.: 10/121,689

(22) Filed: Apr. 15, 2002

(65) Prior Publication Data

US 2003/0195483 A1 Oct. 16, 2003

(51) Int. Cl.⁷ .................................................. A61F 5/44
(52) U.S. Cl. ................... 604/329; 604/329; 604/385.01
(58) Field of Search ............................ 604/329, 385.02, 604/385.01, 385.06; 4/144.1–144.4

(56) References Cited

U.S. PATENT DOCUMENTS

| | | | | |
|---|---|---|---|---|
| 2,878,486 A | * | 3/1959 | Bartlett et al. ................. 4/110 |
| 4,453,938 A | * | 6/1984 | Brendling .................. 604/346 |
| 4,531,245 A | * | 7/1985 | Lowd et al. ................. 4/144.3 |
| 4,681,573 A | * | 7/1987 | McGovern et al. ......... 604/329 |
| 4,756,029 A | * | 7/1988 | Zieve et al. ................. 72/205 |
| D310,124 S | * | 8/1990 | Knowles ....................... D24/54 |
| 5,370,637 A | * | 12/1994 | Brodeur ..................... 604/329 |
| 5,401,263 A | * | 3/1995 | Cornellier ................... 604/329 |
| 5,408,703 A | * | 4/1995 | Cicio ........................... 4/144.2 |
| 5,966,748 A | * | 10/1999 | Young et al. ............... 4/144.4 |
| 6,202,225 B1 | * | 3/2001 | Beck et al. .................. 4/144.2 |
| 6,327,716 B1 | * | 12/2001 | Kaus ........................... 4/144.4 |
| 6,475,198 B1 | * | 11/2002 | Lipman et al. ............. 604/329 |

\* cited by examiner

Primary Examiner—Weilun Lo
Assistant Examiner—Jacqueline F Stephens
(74) Attorney, Agent, or Firm—Troxell Law Office PLLC

(57) ABSTRACT

A urine guide device for females having a urine guide body made of biodegradable material having a first and a second opening portion for receiving and draining urine respectively, wherein the first opening portion is much larger than the second opening portion, therefore, when a female user is urinating the urine will flow into the urine guide body through the first opening portion and out of the second opening portion. The improvement of the device is having a protruding rim extending adjacent to the first opening portion to closely and comfortably conform to an exterior of a pubic area of a female, a bendable member positioned between the first and the second opening portion, for changing the direction of urine draining from the second opening portion, and at least a wiping pad made of absorbent material extending from the periphery of the first opening portion for wiping and preventing slopping urine.

12 Claims, 16 Drawing Sheets

URINE GUIDE DEVICE FOR FEMALES

FIELD OF THE INVENTION

The present invention relates to a urine guide device for females, particularly, to a urine guide device for females in urinating from a standing position, and further for wiping and preventing slopping urine.

BACKGROUND OF THE INVENTION

Most of the traditional urine guide device for females is not available for portability, or not available for wiping and preventing urine slopping; therefore, it is important to have improvement. For example, the prior art of U.S. Pat. No. 5,267,988 discloses a non-invasive female urine collection device, which includes an elongated pad adapted to be positioned comfortably between the legs of a female patient and against the patient's perineal area. Said elongated pad comprises a flat, planar base having an outlet extending between an inner surface and an outer surface thereof. And the pad further comprises a flexible membrane positioned above the inner surface of the base and has an outer circumferential edged to the base. The flexible membrane has an inner circumferential edge that defines an open area therein, with the inner circumferential edge of the flexible membrane surrounding and adjacent, and attached to the inner surface of the base. The inner circumferential edge and outer circumferential edge of the flexible membrane are spaced apart from each other that a chamber is formed between the flexible membrane and the base. The chamber can be inflated and form a comfortable cushion. A portion of the flexible membrane adjacent the inner circumferential edge forms a flow channel that extends from an opening at an outer surface of the membrane to the outlet. The opening of the flow channel at the flexible membrane outer surface is adapted configured to surround the female's urethra. And the device further includes inflation means for inflating the chamber. The prior art has the function of draining the urine, however, it is more complex such as the high cost of some assisting means for comfortably using (the inflation means for inflating the chamber), besides, it is not foldable for carrying. All the above drawbacks avoid females to use it.

Moreover, it is a big problem for females to use an unclean toilet; therefore, they must be very careful when using the toilet such as balancing themselves over a toilet seat or clean the seat with many papers to avoid all contact with the seat. It takes time and resources (such as wasting papers). Besides, when using the public toilet might cause illness due to the polluted water in the toilet may be slopped onto the user when urinating closing to the toilet; thus, it is important to provide a urine guide device for females personal use only and using comfortably with standing position. Another urine guide device for females, such as U.S. Pat. No. 5,893,176, discloses a female urine device to direct the discharge of urine while standing, which incorporates an inner sealing ring adapted to surround and sealingly engage the exterior of the labia majority, an outer sealing ring lying adjacent the inner sealing ring and being adapted to surround and sealingly engage the exterior of the labia majority, and a funnel located below the inner and outer sealing rings and adapted to direct the discharge of urine. However, it is not foldable for carrying, besides, it doesn't has the function of wiping and preventing the slopping urine; therefore, it is not useful for females.

Please refer to the FIG. 1, which shows another conventional urine device for females. Traditionally, the urine device for females comprises a containing member 1 having a first opening portion 11 and a second opening portion 12. When a woman urinates while standing, the urine may flow into the containing member 1 from the first opening portion 11, and drain out from the second opening portion 12. However, this device does not provide any means for preventing and cleaning the slopping urine. Besides, the shape of the first opening portion is very sharp, so it may cause the skin of the exterior of the female's pubic area getting hurt when the first opening portion 11 is surrounding and conforming to the female's pubic area. Furthermore it may not be used for changing the draining direction from the second opening portion 12; thus, user has to use it in a specific direction.

Under the Patent Cooperation Treaty International Publication Number: WO 00/15166 "A disposable funnel-like urinary device for use by a standing female", referring to the FIG. 2, it shows a conventional urinary device comprising a punched sheet of a relatively flexible for obtaining a foldable funnel-like arrangement 2, particularly said funnel-like arrangement 2 including two identical rear rounded flaps 201 and 202 extending inclined with periphery of a larger end 21 for securing urine leakages which can result in the user's clothing being soiled. When a female user uses the urinary device for urinating, the urine flows into the foldable funnel-like arrangement 2 from the larger end 21 and drains out from a smaller end 22, and the flaps 201 and 202 may provide securing means for preventing urine leakages. Such urinary device is foldable for portability; however, the periphery of the larger end 21 is very sharp. Thus, it is not useful because it may cause the skin of the exterior of the female's pubic area getting hurt when the larger end 21 is surrounding and conforming to the female's pubic area.

The U.S. Pat. No. 5,966,748, "Tinkle Safe" discloses a female urination device, please referring to the FIG. 3, which comprising a first end 31 having a opening for receiving urine, a second end 32 having an opening for discharging urine, said opening in said first end 31 being larger than said opening in said second end 32. Said first end 31 having a flap 30 adjacent said opening in said first end 31 and a pad 301 being attached to said flap 30 for sanitary wiping. When a female user uses the urination device to urinate, that allows the user to urinate from a standing position and is a funnel shaped device with an opening at one end 31 that is contoured to the shape of female body and a second end 32 which is smaller than the first end 31 and has an opening to funnel the urine away from the user. In addition, the first end has a sanitary wiping pad attached thereto. Yet, the shape of the first end 31 is not conforming to the exterior of the female's pubic area and not having any security means, so it may cause the urine slopping.

SUMMERY OF THE INVENTION

The present invention provides a urine guide device for females in urinating, which comprises a urine guide body made of biodegradable material having a first and a second opening portion for containing and draining the urine respectively, wherein said first opening portion is much larger than said second opening portion, therefore, when a female user is urinating, the urine will flow into the urine guide body from the first opening portion and out of the urine guide body from the second opening portion. The improvement of said device comprises a protruding rim extending adjacent to said first opening portion and closely and comfortably conforming to the exterior of the pubic area of a female, a bendable member for changing the direction of urine draining from said second opening portion, wherein said bendable member is positioned between said first and second opening portion, and at least a wiping pad made of absorbent material extending from the periphery of said first opening portion for wiping and preventing slopping urine.

BRIEF DESCRIPTION OF THE DRAWINGS

FIGS. 6A-1 and 6B-1 are perspective views of a urine guide device for females in accordance with another embodiment of the present invention.

FIG. 6A-2 is a sectional view of the embodiment of the present invention taken along line IV—IV in FIG. 6A-1.

FIG. 6B-2 is a sectional view of the embodiment of the present invention taken along line IV—IV in FIG. 6B-1.

DESCRIPTION OF THE PREFERRED EMBODIMENTS

The following descriptions of the preferred embodiments are provided to understand the features and the structures of the present invention.

Figure 4A:
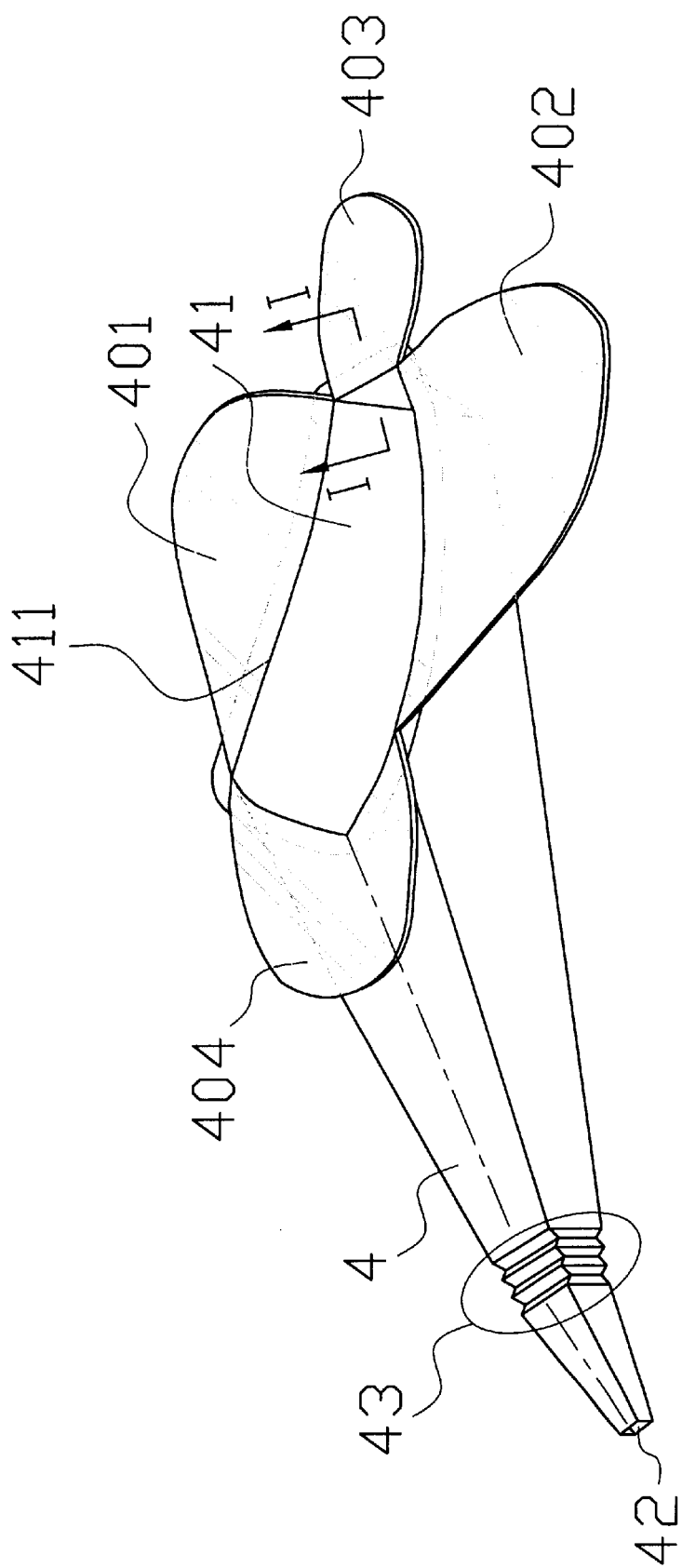
FIG. 4A is a perspective view of a urine guide device for females in accordance with one embodiment of the present invention.
Figure 4B:
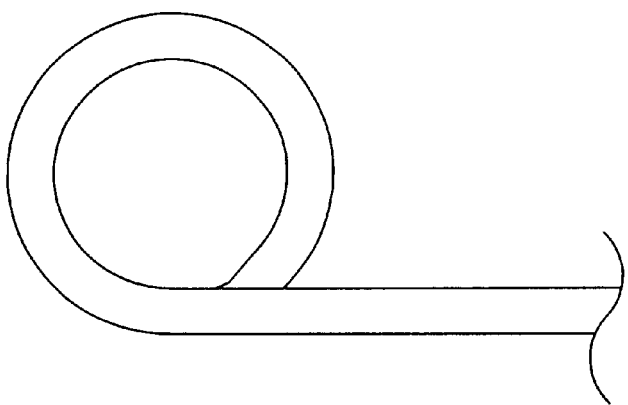
FIG. 4B is a sectional view of the embodiment of the present invention taken along line I—I in FIG. 4A.
Figure 4C:
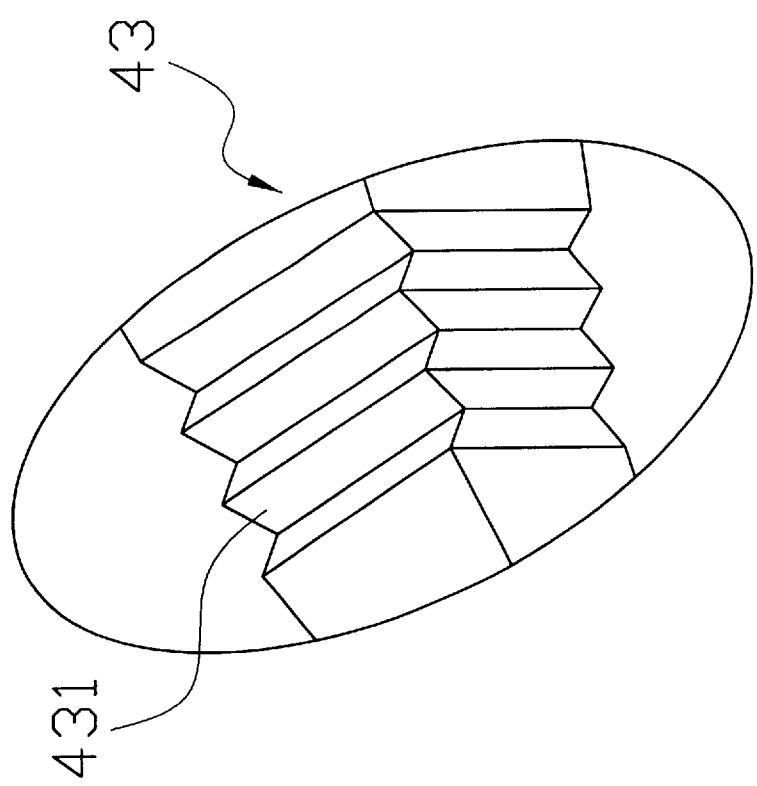
FIG. 4C is an enlarged perspective view of a portion of the embodiment of the present invention in FIG. 4A.
Figure 8:
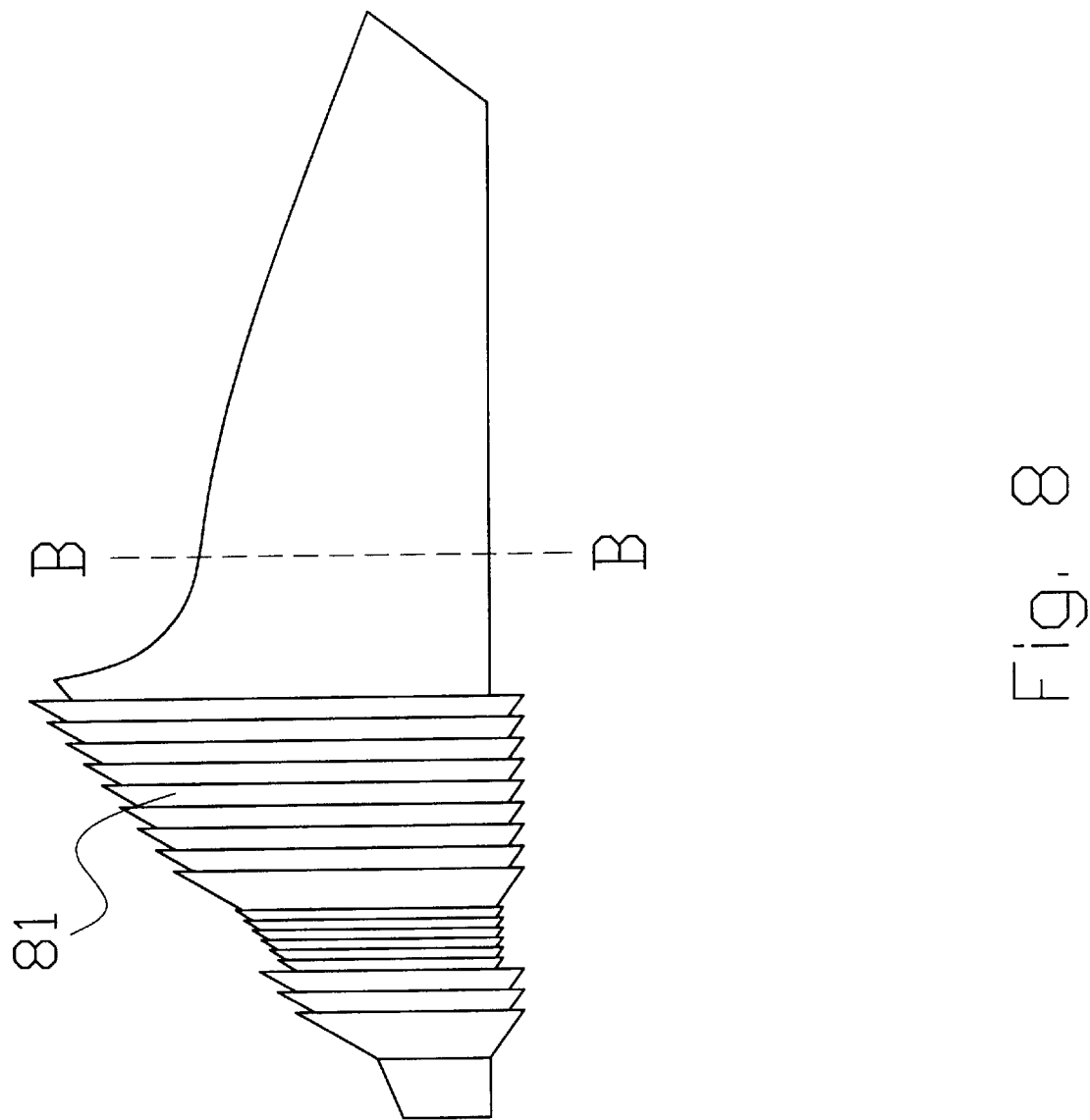
FIG. 8 is a side section view of the present invention after folding.
Figure 9:
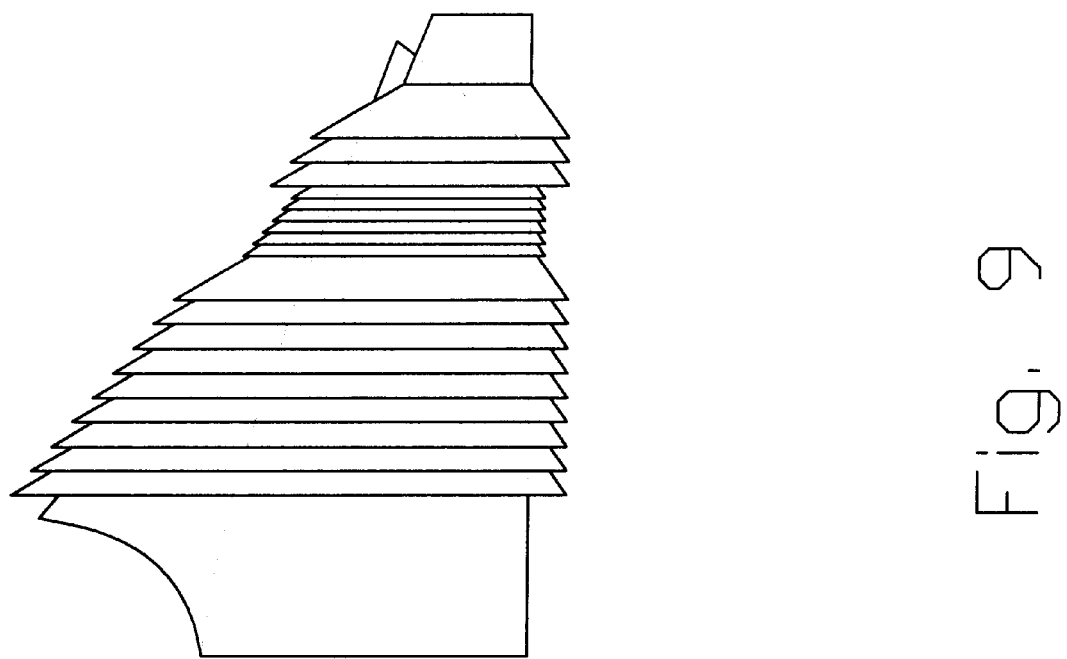
FIG. 9 is another side section view of the present invention after folding in a pocket size.

The present invention "Urine Guide Device for Females", referring to the FIGS. 4A–C, comprises a urine guide body 4 made of biodegradable material having a first and a second opening portions 41 and 42 for containing and draining the urine respectively, wherein said first opening portion 41 is much larger than said second opening portion 42, therefore, when a female user is urinating, the urine will flow into the urine guide body 4 from the first opening portion 41 and out of the urine guide body 4 from the second opening portion 42. The improvement of said device comprises a protruding rim 411 (referring to the I—I cross section) extending adjacent to said first opening portion 41 and closely and comfortably conforming to the exterior of the pubic area of a female, which may provide a protection with the protruding rim 411 for using comfortable. The urine guide body 4 further includes a bendable member 43 with a plurality of pleats 431 for changing the direction of urine draining from said second opening portion 42, wherein said bendable member 43 is positioned between said first and said second opening portion 41 and 42. Moreover, it also provides at least a wiping pad 401, 402, 403, or 404 made of absorbent material extending from the periphery of said first opening portion 41 for wiping and preventing slopping urine. For going out using, this invention may be folded, and furthermore, it may be folded into a plurality of pleats 81, as shown in FIG. 8 and FIG. 9, for portability; wherein the FIG. 9 shows a pocket size after folding inclined with the B—B line for portability.

Figure 1:
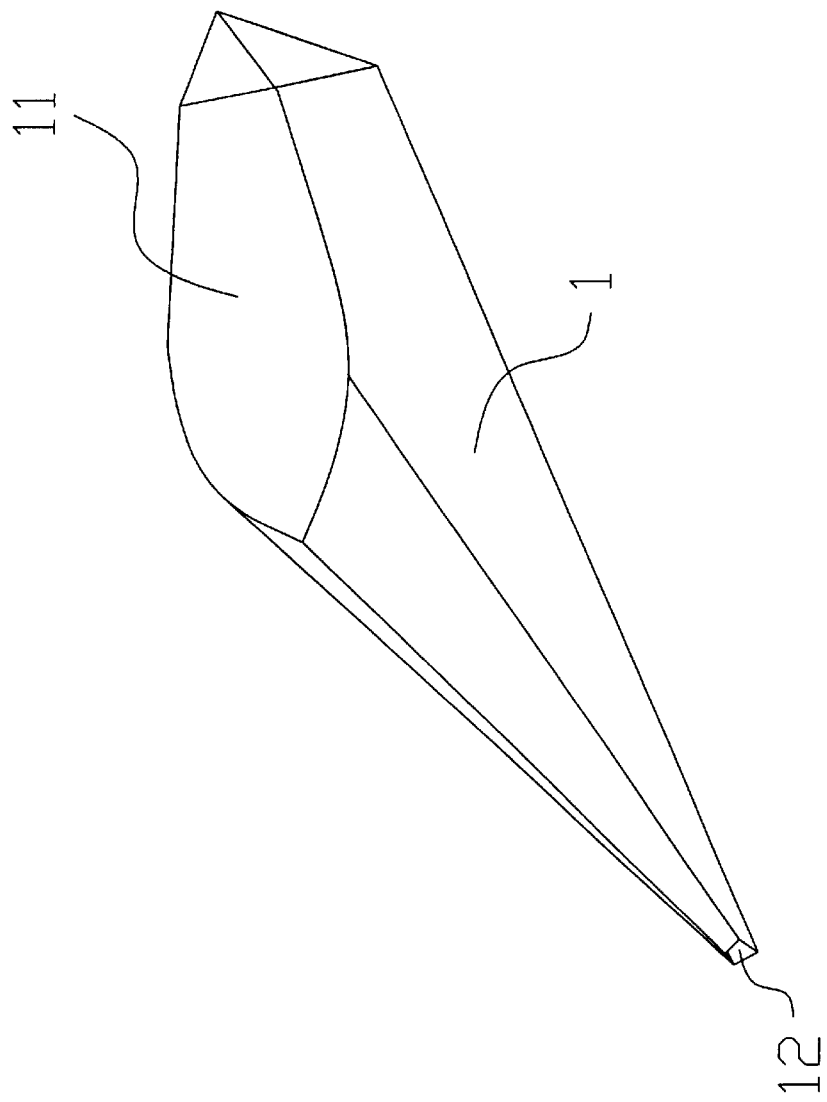
FIG. 1~FIG. 3 are perspective views of conventional urine guide device for females.
Figure 2:
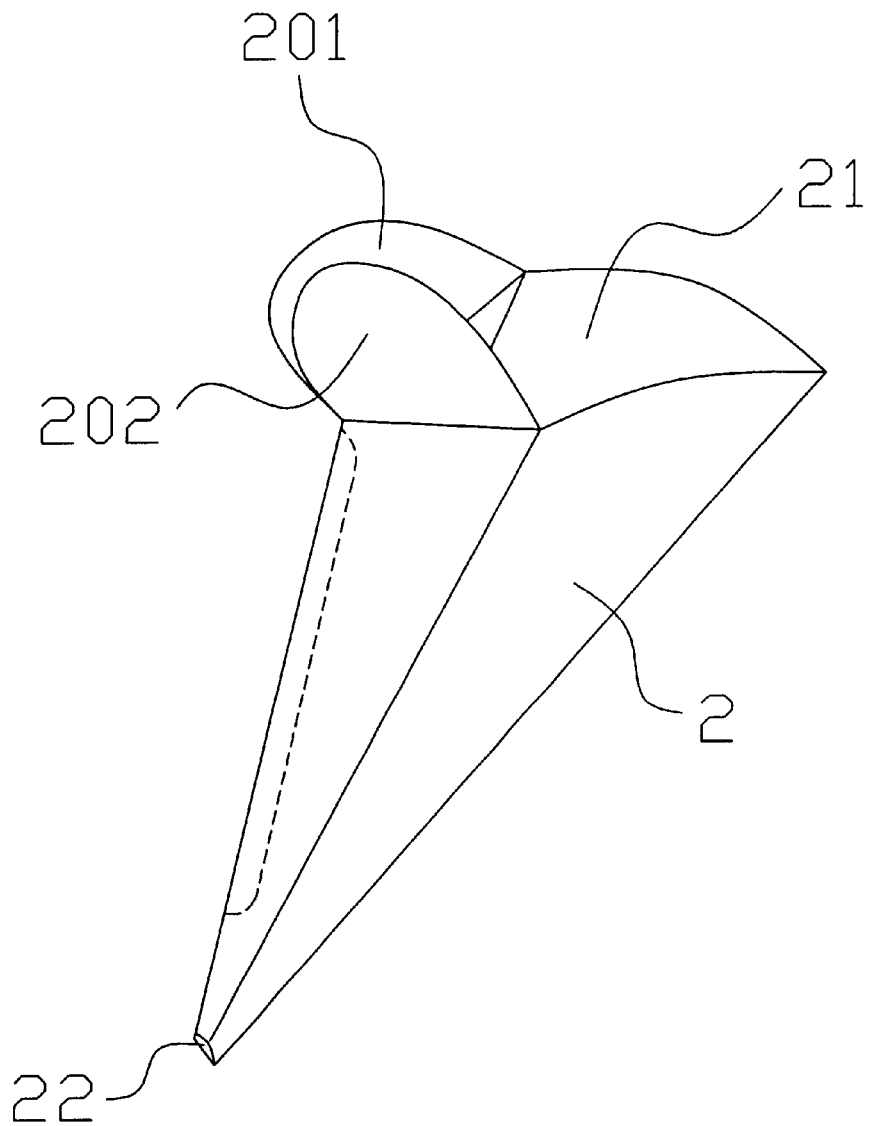
Figure 3:
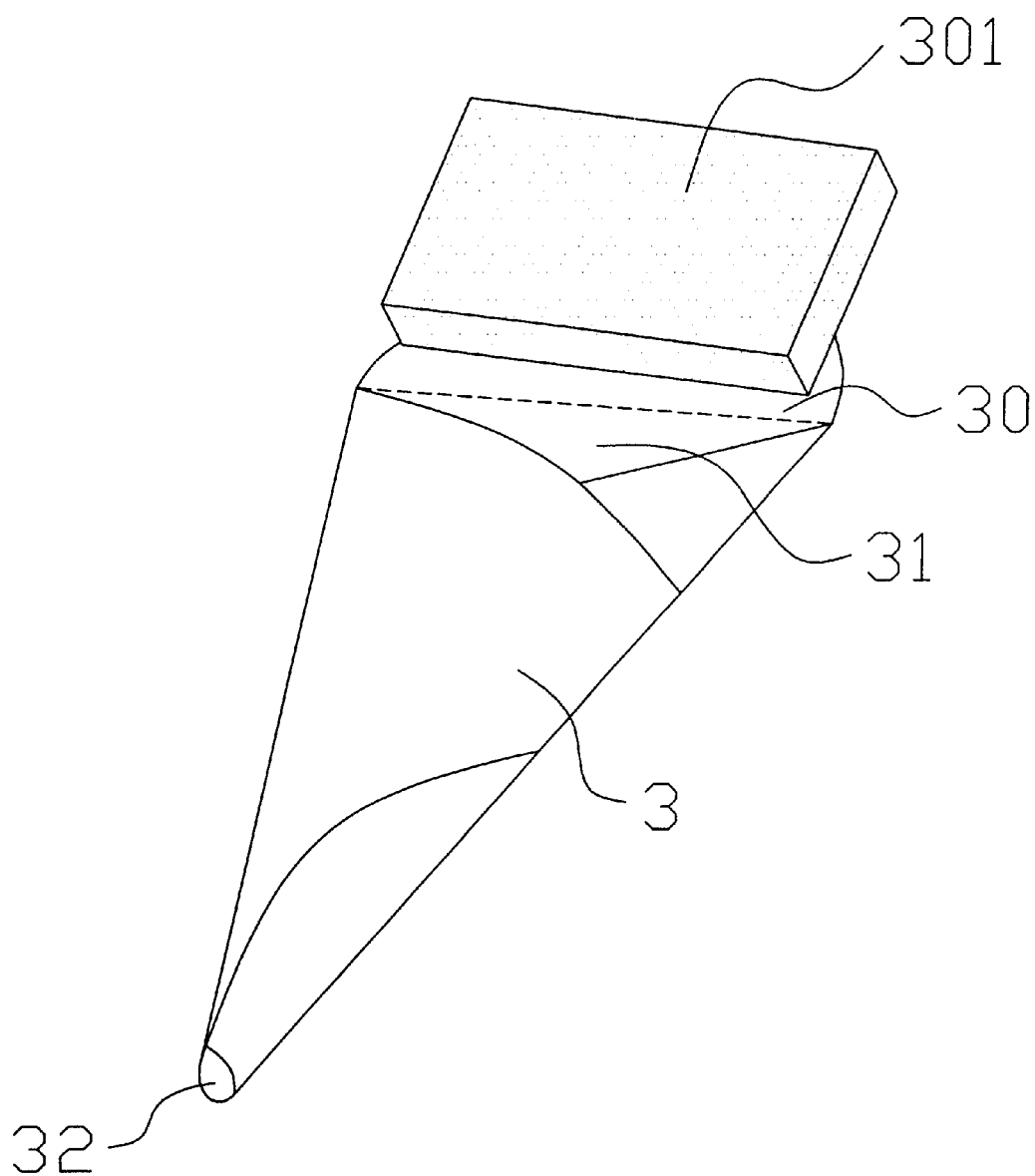
Figures 1, 6A:
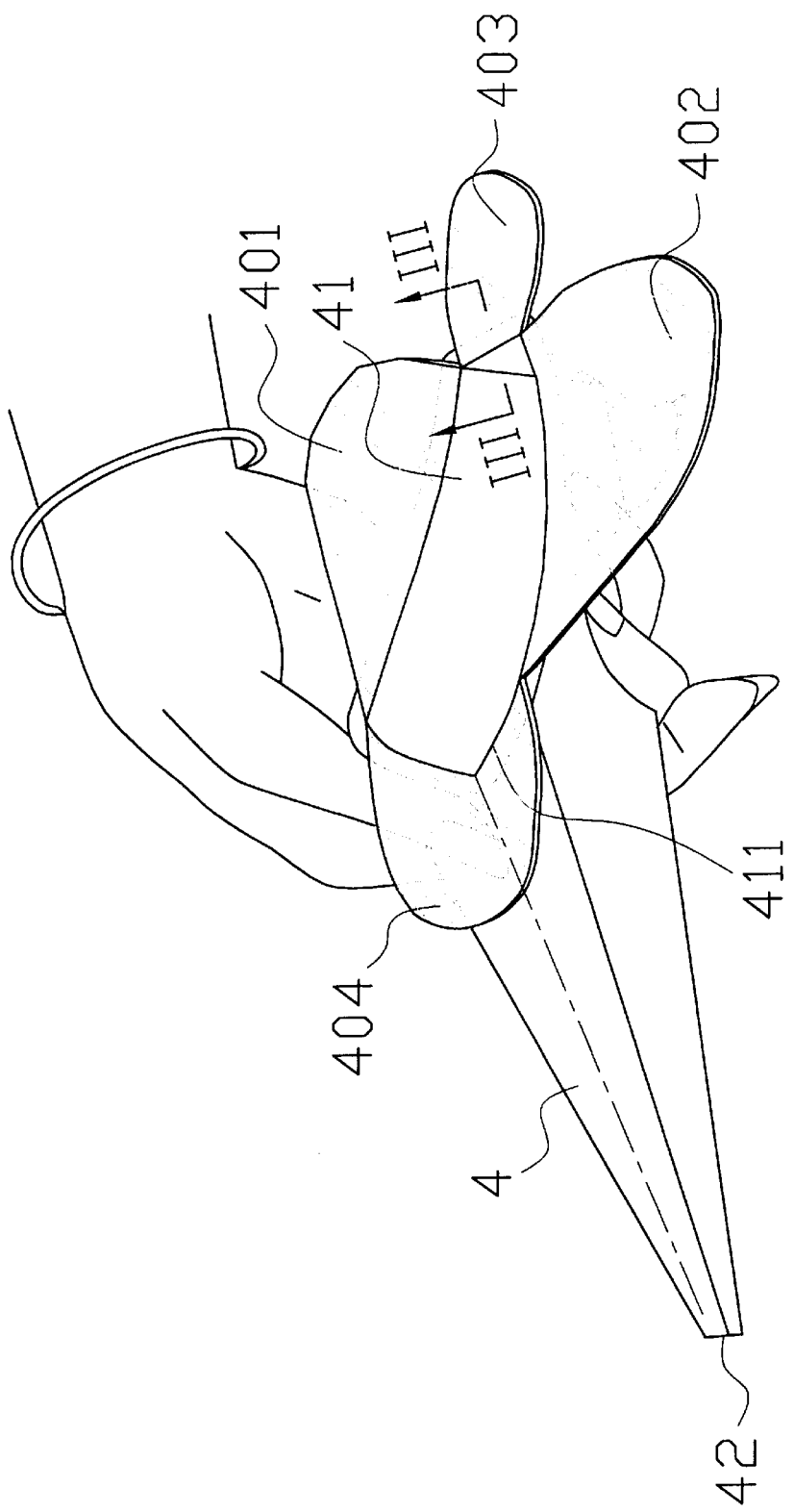
Figures 2, 6A:
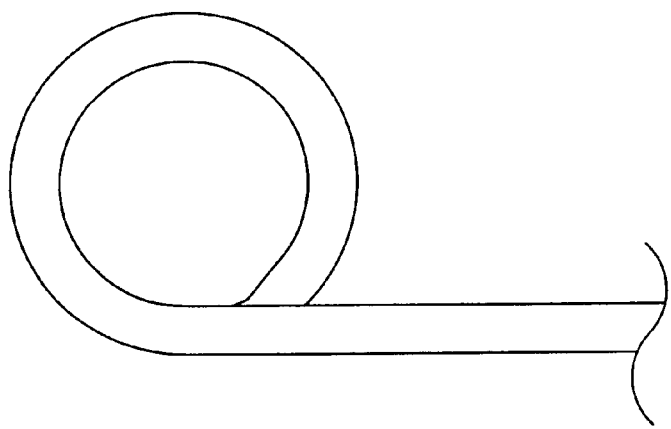
Figures 1, 6B:
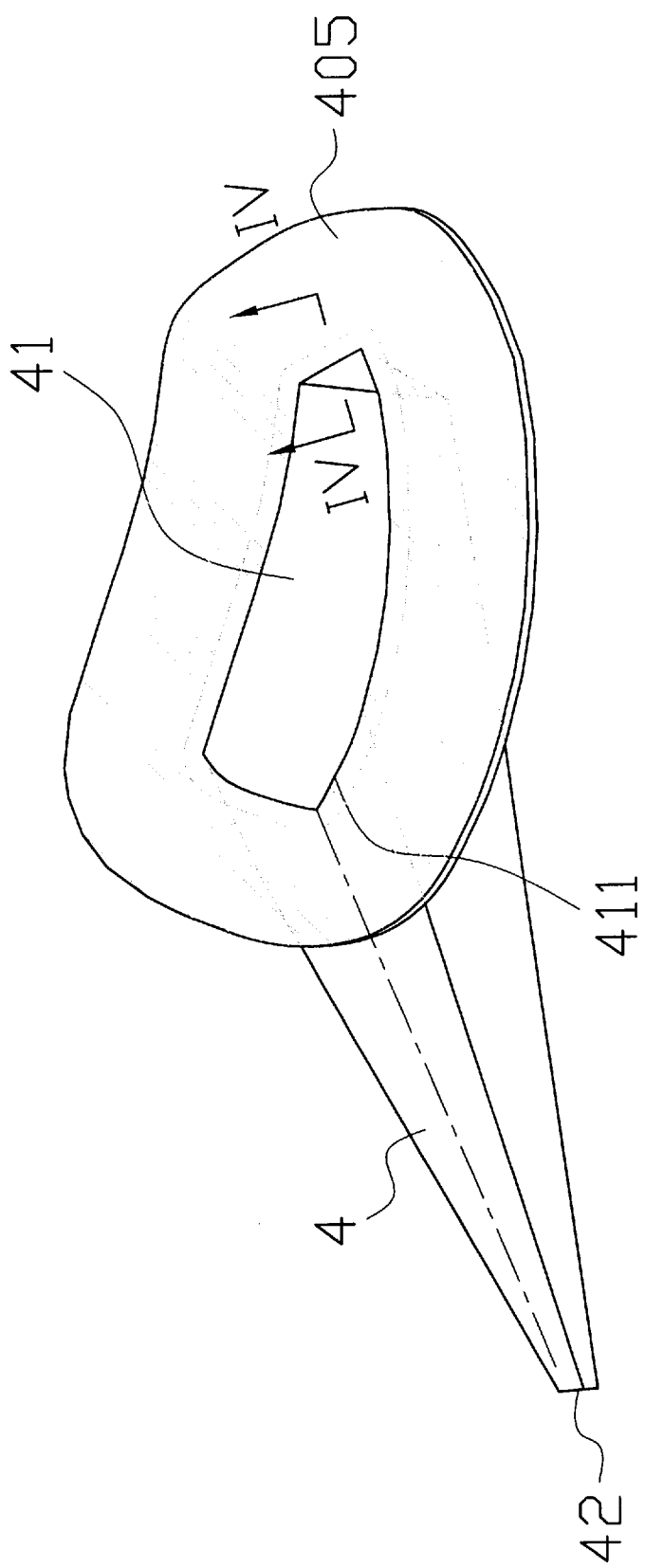
Figures 2, 6B:
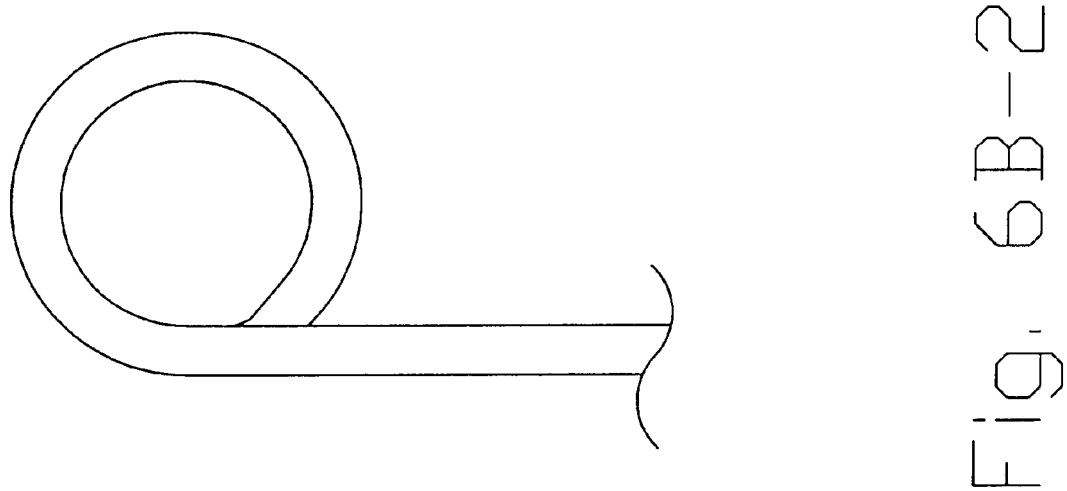

The consideration of manufacturing this invention, the wiping pad may be formed in a various shape with one punch (as the pad 405, shown in the FIG. 6B-1), and then attached to the urine guide body 4. The formation of the wiping pads 401 and 402 may be formed as FIGS. 6A-1 and 6A-2, extending oppositely and separately beside the periphery 411 of said first opening portion 41 for wiping and preventing sloping urine. Or, the wiping pad 403 may extend in back of the periphery 411 of said first opening portion 41 for wiping and preventing sloping urine. Alternatively, the wiping pad 404 may extend in front of the periphery 411 of said first opening portion 41 for wiping and preventing slopping urine.

Figure 5A:
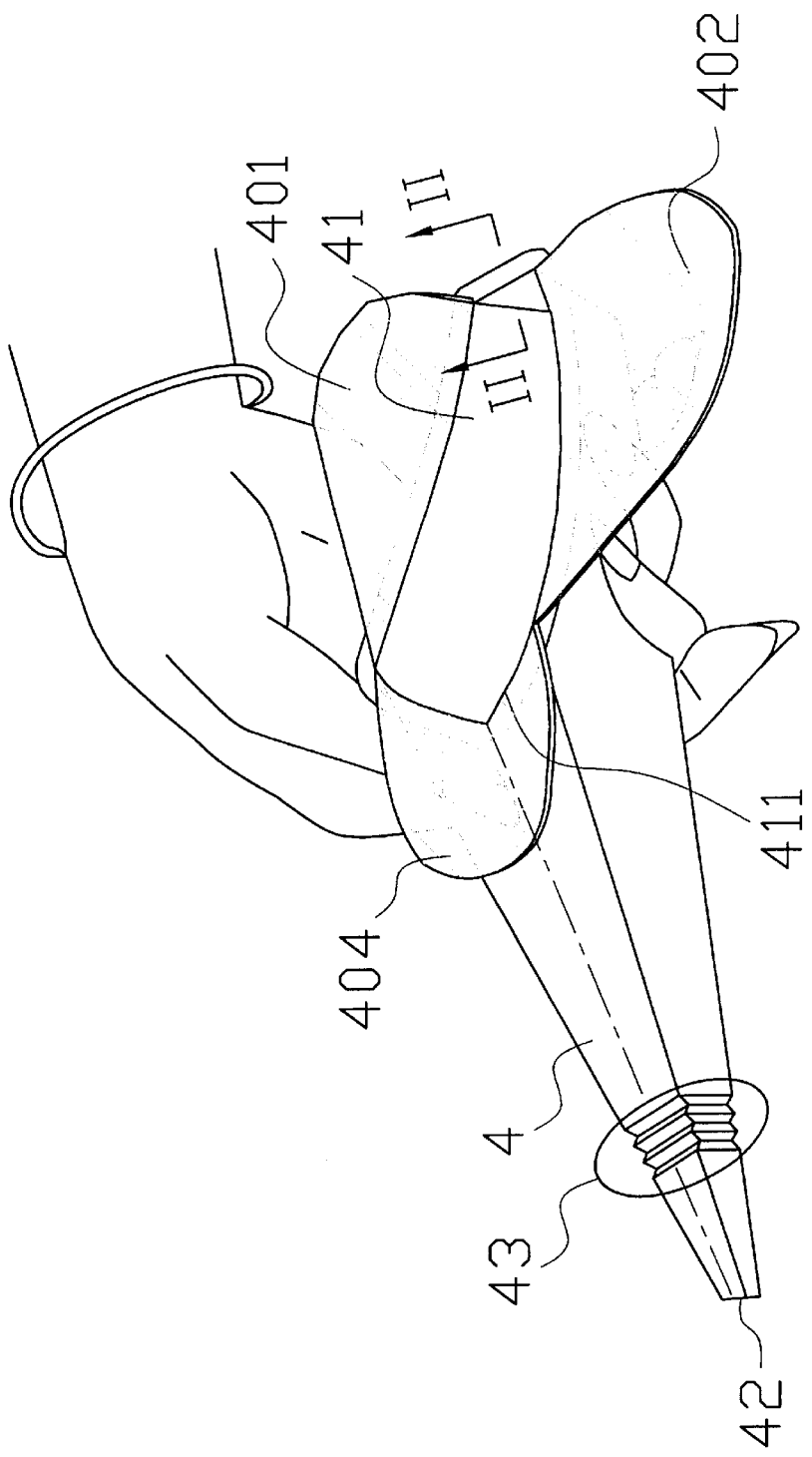
FIG. 5A is a perspective view of a urine guide device for females in accordance with another embodiment of the present invention.
Figure 5B:
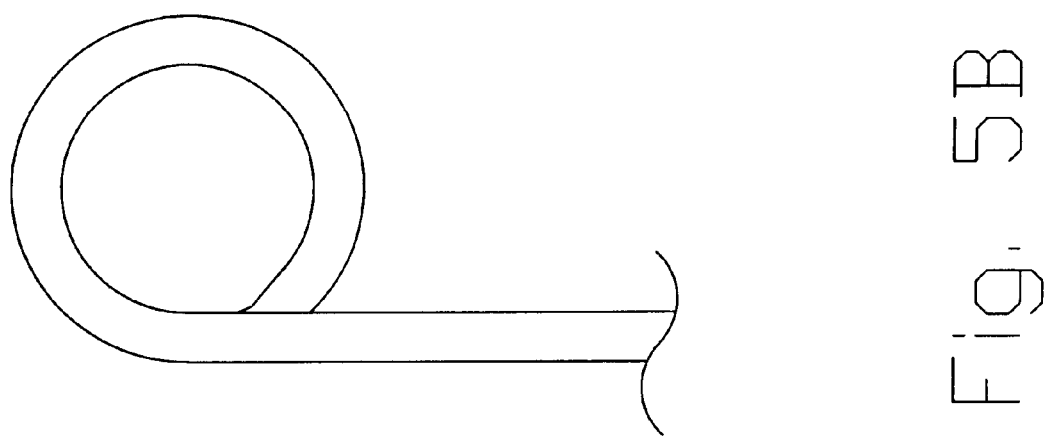
FIG. 5B is a sectional view of the embodiment of the present invention taken along line II—II in FIG. 5A.
Figure 5C:
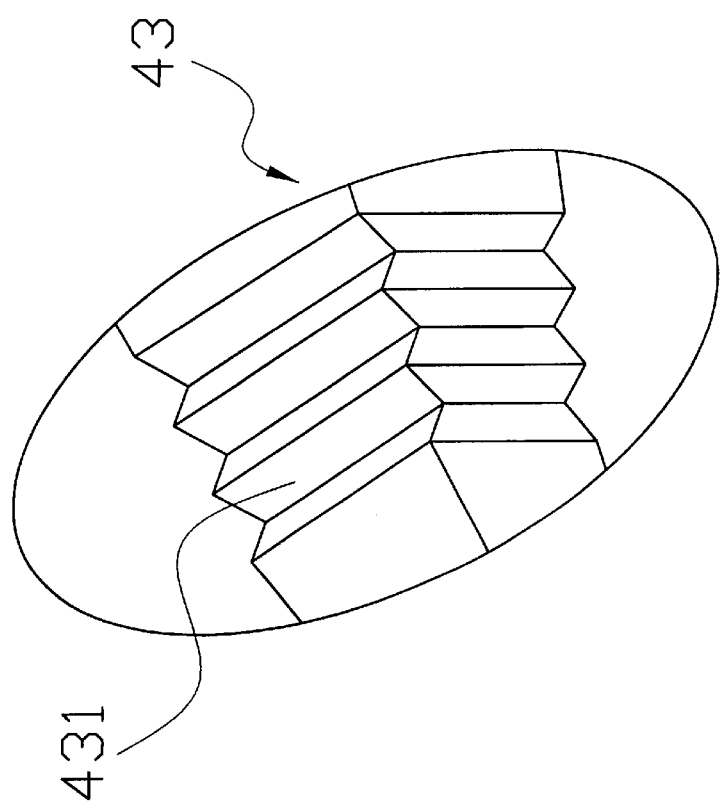
FIG. 5C is an enlarged perspective view of a portion of the embodiment of the present invention in FIG. 5A.
Figure 7:
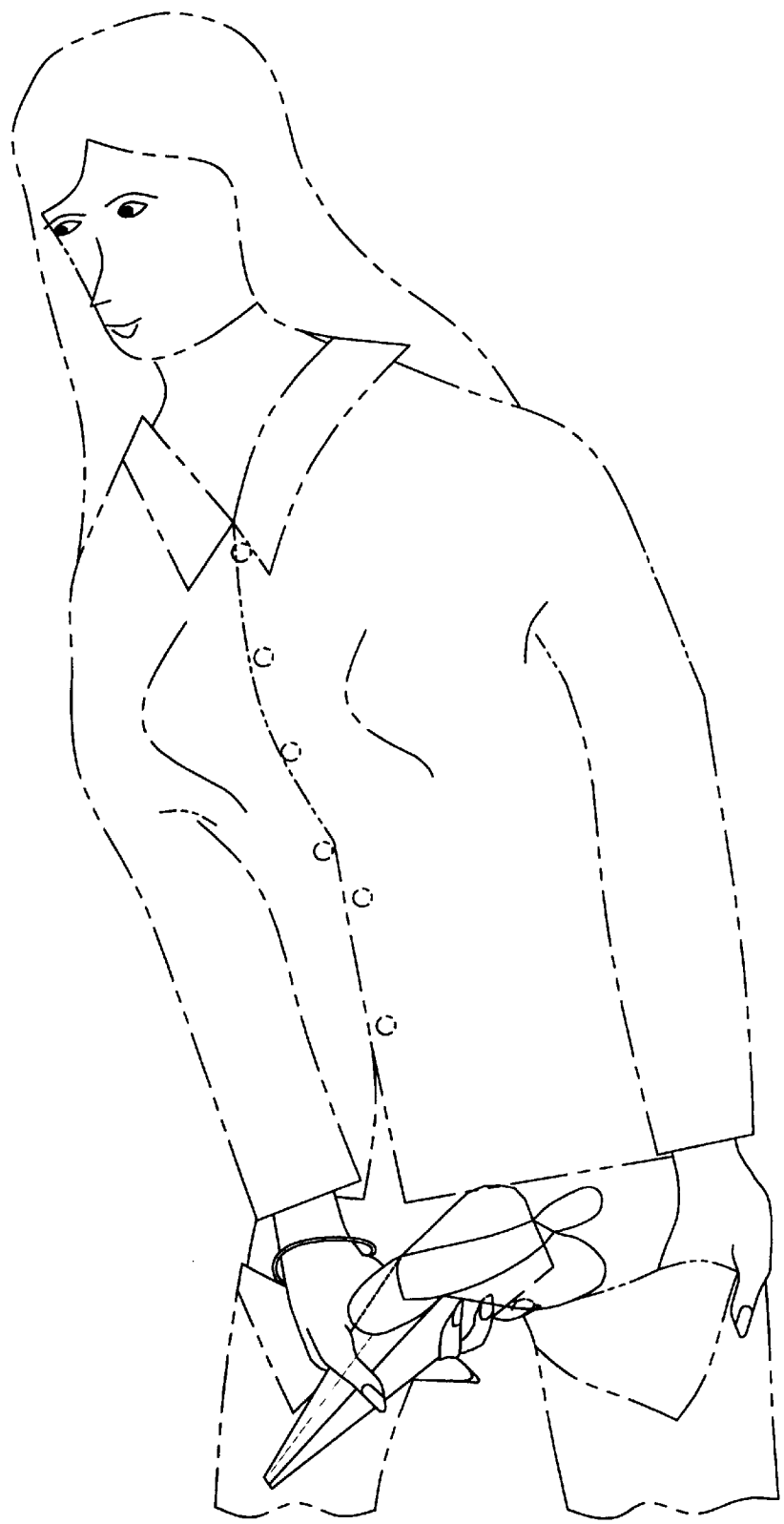
FIG. 7 is an outer plan view showing how the urine guide device may be applied to the body of a woman.

Referring to the FIGS. 5A–C, it shows another preferred embodiment, which comprises a urine guide body 4 made of biodegradable material having a first and s second opening portions 41 and 42 for containing and draining the urine respectively, wherein said first opening portion 41 is much larger than said second opening portion 42, therefore, when a female user is urinating, the urine will flow into the urine guide body 4 from the first opening portion 41 and out fo the urine guide body 4 from the second opening portion 42. The improvement of said device comprises a protruding rim 411 (referring to the II—II cross section) extending adjacent to said first opening portion 41 and closely and comfortably conforming to the exterior of the pubic area of a female (as shown in the FIG. 7), which may provide a protection with the protruding rim 411 for using comfortable. The urine guide body 4 further includes a bendable member 43 with a plurality of pleats 431 for changing the direction of urine draining from said second opening portion 42, wherein said bendable member 43 is positioned between said first and said second opening portion 41 and 42. Moreover, it also provides at least a wiping pad made of absorbent material extending from the periphery 411 of said first opening portion 41 for wiping and preventing slopping urine. For going out using, this invention may be folded, and furthermore, it may be folded into a plurality of pleats 81, as shown in the FIG. 8 and FIG. 9, for portability; wherein the FIG. 9 shows a pocket size after folding inclined with the B—B line for portability.

Referring to the FIGS. 6A-1, 6A-2, 6B-1 and 6B-2, the urine guide device for females in accordance with the present invention comprises a urine guide body 4 made of biodegradable material having a first and a second opening portions 41 and 42 for containing and draining the urine respectively, wherein said first opening portion 41 is much larger than said second opening portion 42, therefore, when a female user is urinating, the urine will flow into the urine guide body 4 from the first opening portion 41 and out of the urine guide body 4 from the second opening portion 42. The improvement of said device comprises a protruding rim 411 (referring to FIGS. 6A-2 and 6B-2) extending adjacent to said first opening portion 41 and closely and comfortably conforming to the exterior of the pubic area of a female (as shown in the FIG. 7), which may provide a protection with the protruding rim 411 for using comfortable. Moreover, it also provides at least a wiping pad made of absorbent material extending from the periphery 411 of said first opening portion 41 for wiping and preventing slopping urine. The consideration of manufacturing this invention, the wiping pad may be formed in a various shape with one punch (as the pad 405, shown in the FIG. 6B-1), and then attached to the urine guide body 4. The formation of the wiping pads 401 and 402 may be formed as FIGS. 6A-1 and 6A-2, extending oppositely and separately beside the periphery 411 of said first opening portion 41 for wiping and preventing slopping urine. Or, the wiping pad 403 may extend in back of the periphery 411 of said first opening portion 41 for wiping and preventing sloping urine. Alternatively, the wiping pad 404 may extend in front of the periphery 411 of said first opening portion 41 for wiping and preventing slopping urine.

For going out using, this invention may be folded, and furthermore, it may be folded into a plurality of pleats 81, as shown in the FIG. 8 and FIG. 9, for portability; wherein the FIG. 9 shows a pocket size after folding inclined with the B—B line for portability.

In summation of the foregoing section, the improved urine guide device for females of the invention therein is an invention of reasonable perfection that not only possesses outstanding practicality, but has an protruding rim for using comfortable and, furthermore, the wiping pad is used for sanitary wiping and the bendable member for changing the urine draining direction is progressive and not only a conception based on familiarity of utilization; therefore, the invention herein fully complies will all new patent application requirement and is hereby submitted to the patent bureau for review and the granting of the commensurate patent rights.

The present invention may be embodied in other specific forms without departing from the spirit of the essential attributes thereof; therefore, the illustrated embodiment should be considered in all respects as illustrative and not restrictive, reference being made to the appended claims rather than to the foregoing description to indicate the scope of the invention.

What is claimed is:

1. A urine guide for use by females when urinating comprising:
   a) a urine guide body having:
      i) a first opening,
      ii) a second opening, and
      iii) a bendable member having a plurality of pleats between the first opening and the second opening for changing the direction of urine flowing from the second opening,
      the urine guide body being made of biodegradable material, the first opening being larger than the second opening;
   b) a protruding rim extending along a periphery of the first opening and adapted for use with an exterior pubic area of a female; and
   c) at least one wiping pad connected to the periphery of the first opening,
   wherein the at least one wiping pad includes two wiping pads connected on opposite sides of the periphery of the first opening.

2. The urine guide for use by females when urinating, according to claim 1, wherein the at least one wiping pad includes a third wiping pad connected to a front of the periphery of the first opening.

3. The urine guide for use by females when urinating, according to claim 1, wherein the urine guide body is foldable.

4. The urine guide for use by females when urinating, according to claim 1, wherein the urine guide body has a plurality of pleats such that the urine guide body is foldable.

5. A urine guide for use by females when urinating comprising:
   a) a urine guide body having:
      i) a first opening,
      ii) a second opening, and
      iii) a bendable member having a plurality of pleats between the first opening and the second opening for changing the direction of urine flowing from the second opening,
      the urine guide body being made of biodegradable material, the first opening being larger than the second opening;
   b) a protruding rim extending along a periphery of the first opening and adapted for use with an exterior pubic area of a female; and
   c) at least one wiping pad connected to the periphery of the first opening,
   wherein the at least one wiping pad is connected to a back of the periphery of the first opening.

6. The urine guide for use by females when urinating, according to claim 5, wherein the urine guide body is foldable.

7. The urine guide for use by females when urinating, according to claim 5, wherein the urine guide body has a plurality of pleats such that the urine guide body is foldable.

8. A urine guide for use by females when urinating comprising:
   a) a urine guide body having a first opening and a second opening, the urine guide body being made of biodegradable material, the first opening being larger than the second opening;
   b) a protruding rim extending along a periphery of the first opening and adapted for use with an exterior pubic area of a female; and
   c) at least one wiping pad connected to the periphery of the first opening,
   wherein the at least one wiping pad includes two wiping pads connected on opposite sides of the periphery of the first opening.

9. The urine guide for use by females when urinating, according to claim 8, wherein the urine guide body has a bendable member having a plurality of pleats, the bendable member being between the first opening and the second opening for changing the direction of urine flowing from the second opening.

10. The urine guide for use by females when urinating, according to claim 8, wherein the at least one wiping pad includes a third wiping pad connected to a front of the periphery of the first opening.

11. The urine guide for use by females when urinating, according to claim 8, wherein the at least one wiping pad includes a fourth wiping pad connected to a back of the periphery of the first opening.

12. The urine guide for use by females when urinating, according to claim 8, wherein the urine guide body is foldable.

* * * * *